United States Patent [19]

Schwab

[11] Patent Number: 5,753,249

[45] Date of Patent: May 19, 1998

[54] MATERIALS AND METHODS FOR PEST CONTROL

[75] Inventor: George E. Schwab, La Jolla, Calif.

[73] Assignee: Mycogen Corporation, San Diego, Calif.

[21] Appl. No.: 569,762

[22] Filed: Dec. 8, 1995

[51] Int. Cl.$^6$ .................. A61K 38/44; A01N 25/00
[52] U.S. Cl. ........................ 424/405; 424/94.4
[58] Field of Search ................... 424/405, 94.2, 424/94.4; 435/69.1, 172.1, 189, 190, 252.3, 254.11, 320.1; 514/1; 536/23.2; 800/205

[56] References Cited

U.S. PATENT DOCUMENTS

| | | | |
|---|---|---|---|
| 5,352,451 | 10/1994 | Miller et al. | 424/93.2 |
| 5,501,976 | 3/1996 | Borovsky et al. | 435/252.3 |
| 5,558,862 | 9/1996 | Corbin et al. | 424/94.4 |

OTHER PUBLICATIONS

Corbin, D.R. et al. (1994) "Cloning of an Insecticidal Cholestrol Oxidase Gene and Its Expression in Bacteria and in Plant Protoplasts" Applied and Environmental Microbiology 60(12):4239–4244.

Purcell, J.P. et al. (1993) "Cholesterol Oxidase: A Potent Insecticidal Protein Active Against Boll Weevil Larvae" Biochemical and Biophysical Research Communications 196(3):1406–1413.

*Primary Examiner*—Charles L. Patterson, Jr.
*Attorney, Agent, or Firm*—Saliwanchik, Lloyd & Saliwanchik

[57] ABSTRACT

The subject invention concerns methods and compositions for the selective control of pests. The method involves the administration of compounds which act on ecdysteroids or their derivatives or precursors. In a preferred embodiment, plants are transformed to express ecdysone oxidase which controls pests which feed on the transformed plants.

2 Claims, No Drawings

MATERIALS AND METHODS FOR PEST CONTROL

BACKGROUND OF THE INVENTION

Insects cost farmers billions of dollars annually in crop losses and in the expense of keeping these pests under control. The losses caused by insect pests in agricultural production environments include decrease in crop yield, reduced crop quality, and increased harvesting costs.

Chemical pesticides have provided an effective method of pest control; however, the public has become concerned about the amount of residual chemicals which might be found in food, ground water, and the environment. Therefore, synthetic chemical pesticides are being increasingly scrutinized, and correctly so, for their potential toxic environmental consequences. Synthetic chemical pesticides can poison the soil and underlying aquifers, pollute surface waters as a result of runoff, and destroy non-target life forms. Synthetic chemical control agents have the further disadvantage of presenting public safety hazards when they are applied in areas where pets, farm animals, or children may come into contact with them. They may also provide health hazards to applicants, especially if the proper application techniques are not followed. Regulatory agencies around the world are restricting and/or banning the uses of many pesticides and particularly the organic synthetic chemical pesticides which are persistent in the environment and enter the food chain. Examples of widely used synthetic chemical pesticides include the organochlorines, e.g., DDT, mirex, kepone, lindane, aldrin, chlordane, aldicarb, and dieldrin; the organophosphates, e.g., chlorpyrifos, parathion, malathion, and diazinon; and carbamates. Stringent new restrictions on the use of pesticides and the elimination of some effective pesticides from the market place could limit economical and effective options for controlling costly pests.

Because of the problems associated with the use of organic synthetic chemical pesticides, there exists a clear need to limit the use of these agents and a need to identify alternative control agents. The replacement of synthetic chemical pesticides, or combination of these agents with biological pesticides, could reduce the levels of toxic chemicals in the environment. A biological pesticidal agent that is enjoying increasing popularity is the soil microbe *Bacillus thuringiensis* (*B.t.*). *Bacillus thuringiensis* is a Gram-positive, spore-forming bacterium characterized by parasporal crystalline protein inclusions. These inclusions often appear microscopically as distinctively shaped crystals. The proteins can be highly toxic to pests and specific in their toxic activity. Certain *B.t.* toxin genes have been isolated and sequenced, and recombinant DNA-based *B.t.* products have been produced and approved for use. In addition, with the use of genetic engineering techniques, new approaches for delivering these *B.t.* endotoxins to agricultural environments are under development, including the use of plants genetically engineered with endotoxin genes for pest resistance and the use of stabilized intact microbial cells as *B.t.* endotoxin delivery vehicles. Until the last ten years, commercial use of *B.t.* pesticides has been largely restricted to a narrow range of lepidopteran (caterpillar) pests. In recent years, however, investigators have discovered *B.t.* pesticides with specificities for a much broader range of pests.

Unfortunately, certain insects are refractory to the effects of *B.t.* and/or insects may develop resistance to *B.t.* The former includes insects such as boll weevil and black cutworm as well as adult insects of most species which heretofore have demonstrated no apparent significant sensitivity to *B.t.* δ-endotoxins. With respect to the latter, resistance management strategies *B.t.* transgene plant technology have ascended to a prominent position. There remains, however, a great need to identify new insect control methods which are effective and also safe for use in the environment.

One possible approach to insect control involves the disruption of vital metabolic functions of the insect. Steroid compounds play an important role in the growth and development of insects. Insects are unable to form the cyclopentanoperhydrophenanthrene ring structure of steroids. As such they are dependent on dietary sources of steroids (cholesterol and/or β-sitosterol) for subsequent elaboration of developmental steroids including ecdysone and 20-hydroxyecdysone. Ecdysone and 20-hydroxyecdysone are pivotal hormones in insect metamorphosis. Ecdysone oxidase mediates the oxidation of ecdysone and 20-hydroxyecdysone to 3-dehydoxyecdysone and 3-dehydro-20-hydroxyecdysone, respectively, plus $H_2O_2$. Insects appear to be unique in this oxidation reaction. The reaction products have marginal molting activity and no other known hormonal activity, thus ecdysone oxidase is believed to participate in inactivation pathways of steroid catabolism. Ecdysone oxidase is localized in the fat body and cytosol of the gut of insects. Studies have shown that exogenously administered ecdysone and 20-hydroxyecdysone can have a profound effect on insect development and may even result in death (Tanaka, 1993).

The gene encoding cholesterol exidase has been cloned into plants (Purcell, 1994; Corbin, 1994). However, mammals are dependent on cholesterol as precursor for the elaboration of steroid hormones (corticosterone, sex hormones, etc.). Such presentation of an active enzyme in planta may present safety issues because of the potential for interference with mammalian steroid elaboration.

BRIEF SUMMARY OF THE INVENTION

The subject invention pertains to novel materials and methods for the control of non-mammalian pests. In a preferred embodiment, the subject invention concerns a method for the control of a non-mammalian pest which comprises administering to said pest an effective amount of an enzyme which acts upon a compound selected from the group consisting of ecdysteroids, and derivatives and precursors of ecdysteroids. Specifically exemplified herein is the use of the enzymes ecdysone oxidase and 3-oxoecdysteroid 3β-reductase to control insects, nematodes, and mites.

In one embodiment, the invention concerns administering to non-mammalian pests an effective amount of a compound which disturbs a metabolic pathway involved in ecdysteroid metabolism. The method of the subject invention is particularly advantageous because the pathway which is disturbed does not exist in mammals, and, therefore, the materials and methods of the subject invention are highly selective and are not known to pose any safety risk to humans.

In a preferred embodiment of the subject invention, genes which encode the pesticidal compounds are transformed into, and expressed in, a host with which the pest will come into contact. The host may be, for example, a plant upon which the pest will feed. Alternatively, the host may be a microorganism such as a fungus or bacterium which can then be applied to the location where the pest is to be controlled. The transformed microbes may be alive and chosen so as to colonize the area where pests are to be controlled. Also, the microbe may be killed after the protein is produced, in which case the microbe is simply used to deliver the pesticidal compound.

Use of a protein-based pesticide such as ecdysone oxidase whose mode of action and molecular composition are distinct from that of B.t. provides an excellent alternative to B.t. in resistance management schemes.

DETAILED DISCLOSURE OF THE INVENTION

The subject invention concerns new materials and methods for the safe and effective control of non-mammalian pests. In one embodiment, the subject invention concerns the use of a compound which acts on ecdysteroids, or derivatives or precursors of ecdysteroids. In a particularly preferred embodiment, the subject invention concerns the use of the ecdysone oxidase as a pesticide in planta for control of pests such as insects, mites, and nematodes.

In addition to ecdysone oxidase, the enzyme 3-oxoecdysteroid 3β-reductase, can also be used as a control agent, either alone or co-expressed with ecdysone oxidase. This enzyme also provides selective control of pests without affecting a known mammalian biological pathway. 3-oxoecdysteroid 3β-reductase catalyzes the reduction of the 3-keto group of either 3-dehydroecdysone or 3-dehydro-20-hydroxyecdysone to a 3α-hydroxyl group. These reduction products are void of activity and the reaction is irreversible.

Other pest control compounds useful according to the subject invention include compounds which act on ecdysteroids, or derivatives or precursors of ecdysteroids. Such ecdysteroids include ecdysone; 26-hydroxyecdysone; 2-deoxyecdysone; 3-epi-20-hydroxyecdysone; 22-deoxyecdysone; 3-dehydroecdysone; 20-hydroxyecdysone; 3-dehydro-20-dehydroxyecdysone; 2,14,22,25-tetradeoxyecdysone; 2,22,25-trideoxyecdysone; 2,22-bis-deoxyecdysone; ketol; and ketodiol.

In one embodiment, the methods of the subject invention achieve pest control by the administration to pests of an effective amount of a compound which disturbs the metabolic reactions associated with ecdysteroid compounds. These compounds include enzymes, substrates, and analogs of substrates.

The subject invention is particularly advantageous for the control of pests which are refractory to the effects of *Bacillus thuringiensis* (*B.t.*) and/or pests which develop resistance to *B.t.* Use of a protein-based pesticide such as ecdysone oxidase whose mode of action and molecular structure are distinct from that of *B.t.* provides an excellent alternative to *B.t.* in resistance management schemes.

As used herein, the term "controlling pests" means reducing the number of pests which cause damage. This reduction may be either through mortality, retardation of development (stunting), or reduced reproductive efficiency. Reference to "pests" means non-mammalian pests and includes, for example, insects, nematodes, and mites. Insects would include, for example, all manner of sucking and piercing insects including, for example, dipterans, coleopterans, and lepidopterans. Ecdysteroid compounds are well known in the art, as are the precursors and derivatives of these compounds. See, for example, Gilbert and Goodman, 1981.

The compounds useful according to the subject invention to control pests can be purified from natural sources. Once purified, the compounds can be formulated and applied directly to pests or applied in such a way that pests come into contact with the compounds. Thus, the compounds can be applied generally to surfaces, such as plant surfaces or the surrounding ground where pests are to be controlled. Alternatively, the compounds may be formulated as a bait to be ingested by the pests. These formulated compositions can readily be prepared and applied by a person skilled in the art having the benefit of the current disclosure.

The administration of the pest control compounds of the subject invention can also be accomplished by transforming an appropriate host with a genetic construct which directs the recombinant host to produce the pesticidal compound. The identification, production, and use of such genetic constructs can be carried out by a person skilled in this art having the benefit of the instant disclosure. For example, for a protein isolated as described herein, partial amino acid sequencing can be used for the development of oligonucleotide probes. A cDNA library can be constructed or obtained. The probes can then be used to identify the desired gene within the cDNA library. After sequencing, the gene can be reconstructed for use in planta expression under the control of a suitable promoter.

Genes of interest may be inserted into a transformation vector cassette which is used to transform an appropriate host. In one embodiment, the host may be a plant-colonizing microorganism which, when applied to plants or their surroundings, expresses the genes producing the control compound, such as an ecdysone oxidase, thereby providing control of pests. Alternatively, genes which function in plants and encode the subject compounds may be inserted into transformation vector cassettes which may be incorporated into the genome of the plant, which then protects itself from pest attack by expressing the gene and producing the pest control compound. Additionally, the plant may also be transformed to co-express *B.t.* genes which express proteins for the control of pests.

Thus, one aspect of the subject invention is a method of producing genetically transformed plants which express an effective amount of a pest control compound such as ecdysone oxidase. The method may comprise the steps of:

(a) inserting into the genome of a plant cell a recombinant DNA molecule comprising:
  (i) a promoter which functions in plant cells to cause the production of an RNA sequence;
  (ii) a structural coding sequence that encodes ecdysone oxidase; and
  (iii) a 3' non-translated region which functions in said plant cells to cause the addition of polyadenylate nucleotides to the 3' end of the RNA sequence,
  wherein the promoter is heterologous with respect to the structural coding sequence and wherein the promoter is operatively linked with the structural coding sequence, which is in turn operably linked with the non-translated region;

(b) obtaining transformed plant cells; and (c) regenerating from the transformed plant cells genetically transformed plants which express a pesticidally effective amount of the pest control compound.

A number of promoters which are active in plant cells have been described in the literature. Such promoters may be obtained from plants or plant viruses and include, but are not limited to, the nopaline synthase (NOS) and octopine synthase (OCS) promoters (which are carried on tumor-inducing plasmids of *Agrobacterium tumefaciens*), the cauliflower mosaic virus (CaMV) 19S and 35S promoters, the light-inducible promoter from the small subunit of ribulose 1,5-bisphosphate carboxylase (ssRUBISCO, a very abundant plant polypeptide), and the Figwort Mosaic Virus (FMV) 35S promoter. All of these promoters have been used to create various types of DNA constructs which have been expressed in plants.

Furthermore, materials and methods for introducing genes into plants in order to confer upon such plants the ability to produce pesticidal proteins is well known in the art. In a preferred embodiment, the genes are modified to facilitate optimal stability and expression in the selected plant host. In this regard, U.S. Pat. No. 5,380,831, which pertains specifically to optimization of *B.t.* genes for expression in plants, is incorporated herein by reference.

Genes and proteins. In one embodiment of the subject invention, a gene which encodes a pest control compound can be used to transform a suitable host. The genes useful according to the subject invention include not only the full length sequences but also fragments of these sequence, variants, and mutants, which encode pesticidal compounds. As used herein, the terms "variants" or "variations" of genes refer to nucleotide sequences which encode the same proteins or which encode equivalent proteins having the desired pest-controlling activity. As used herein, the term "equivalent proteins" refers to compounds having the same or essentially the same biological activity against the target pests as the compounds which are specifically disclosed.

It should be apparent to a person skilled in this art that genes encoding the compounds useful according to the subject invention can be obtained through several means. These genes, or portions or variants thereof, may be constructed synthetically, for example, by use of a gene synthesizer. Variations of genes may be readily constructed using standard techniques for making point mutations. Also, fragments of these genes can be made using commercially available exonucleases or endonucleases, or by site-directed mutagenesis, according to standard procedures. For example, enzymes such as Bal31can be used to systematically cut off nucleotide from the ends of these genes. Genes which encode active fragments may also be obtained using a variety of restriction enzymes. Proteases may be used to directly obtain active fragments of these compounds. Genes encoding these equivalent compounds can be derived from DNA libraries using the teachings provided herein.

There are a number of methods for obtaining the compounds useful according to the instant invention. For example, antibodies to enzymes disclosed herein can be used to identify and isolate other enzymes. These antibodies can then be used to specifically identify equivalent enzymes with the characteristic activity by immunoprecipitation, enzyme linked immunosorbent assay (ELISA), or Western blotting. Antibodies to the enzymes disclosed herein, or to equivalent enzymes, or fragments of these enzymes, can readily be prepared using standard procedures in this art. The genes which encode these enzymes can then be obtained.

Fragments and equivalents which retain the enzymatic activity of the exemplified enzymes are within the scope of the subject invention. Also, because of the redundancy of the genetic code, a variety of different DNA sequences can encode these enzymes. It is well within the skill of a person trained in the art to create these alternative DNA sequences encoding the same, or essentially the same, enzymes. These variant DNA sequences are within the scope of the subject invention. As used herein, reference to "essentially the same" sequence refers to sequences which have amino acid substitutions, deletions, additions, or insertions which do not materially affect enzymatic activity.

Recombinant hosts. The genes useful according to the subject invention can be introduced into a wide variety of microbial or plant hosts. Expression of the gene results, directly or indirectly, in the production of the pest-controlling compound. With suitable microbial hosts, e.g., Pseudomonas, the microbes can be applied to the situs of the pest, where they will proliferate and be ingested by the pest, resulting in control of the pest. Alternatively, the microbe hosting the desired gene can be treated under conditions that prolong the activity of the active compound and stabilize the cell. The treated cell, which retains the pesticidal activity, then can be applied to the environment of the target pest.

Where the gene is introduced via a suitable vector into a microbial host, and said host is applied to the environment in a living state, it is advantageous to use certain host microbes. For example, microorganism hosts can be selected which are known to occupy the pest's habitat. Microorganism hosts may also live symbiotically with a specific species of pests. These microorganisms are selected so as to be capable of successfully competing in the particular environment with the wild-type microorganisms, provide for stable maintenance and expression of the gene expressing the desired compound and, desirably, provide for improved protection of the pesticide from environmental degradation and inactivation.

A wide variety of ways are available for introducing the gene of interest into a microorganism host under conditions which allow for stable maintenance and expression of the gene. These methods are well known to those skilled in the art.

Treatment of cells. As mentioned above, recombinant cells expressing a pesticidal compound can be treated to prolong the pesticidal activity and stabilize the cell by forming a cellular microcapsule. The pesticide microcapsule that is formed comprises the active compound within a cellular structure that has been stabilized and will protect the compound when the microcapsule is applied to the environment of the target pest. Suitable host cells may include either prokaryotes or eukaryotes, normally being limited to those cells which do not produce substances toxic to higher organisms, such as mammals. The cell will usually be intact and be substantially in the proliferative form when treated, rather than in a spore form, although in some instances spores may be employed. Methods for treatment of microbial cells are disclosed in U.S. Pat. Nos. 4,695,455 and 4,695,462, which are incorporated herein by reference.

Growth of cells. The cellular host containing the gene of interest may be grown in any convenient nutrient medium, where the DNA construct provides a selective advantage, providing for a selective medium so that all, or substantially all, of the cells retain the gene. These cells may then be harvested in accordance with conventional ways. The recovered microbes can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations. Formulated bait granules containing an attractant and either the pest-controlling compound or recombinant microbes comprising the genes encoding the compound, can be applied to the environment of the pest. The bait may be applied liberally since the control compounds do not affect known biological pathways of animals or humans. The product may also be formulated as a spray or powder. A recombinant host expressing the control compounds gene may also be incorporated into a bait or food source for the pest.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids. Formulations that contain cells will generally have from about $10^2$ to about $10^4$ cells/mg. These formulations will be administered at about 50 mg (liquid or dry) to 1 kg or more per hectare.

The formulations can be applied to the environment of the pests, e.g. on plant foliage.

Following are examples which illustrate procedures, including the best mode, for practicing the invention. These examples should not be construed as limiting. All percentages are by weight and all solvent mixture proportions are by volume unless otherwise noted.

EXAMPLE 1

Purification of Ecdysone Oxidase

*Manduca sexta* (tobacco hornworm) larvae of mixed sexes can be reared at ambient temperature (20°–25° C.) and relative humidity (50–60%) on artificial diet. One to two weeks after ecdysis to the fifth instar, the larvae can be chilled on ice and dissected. Unless noted otherwise, all the following procedures can be conducted at 4° C. The midguts of 30–50 larvae can be collected, placed in three volumes of homogenization buffer (50 mM Tris-HCl, pH 7.0, 1 mm $Na_2$-ethylenediamine tetraacetic acid ($Na_2$-EDTA), 10 μM leupeptin and 0.1 mM dithiothreitol (DTT) and homogenized using a Potter-Elvejum, Teflon-glass homogenizer. The homogenate can be centrifuged (10 k Xg×30 minutes) and the pellet discarded. The supernatant can be sonicated for 30 seconds at 80% output (Branson Sonifier 450, CT) and the supernatant material centrifuged (105 k Xg×90 minutes). The microsomal pellet can be discarded, and the supernatant can be retained and the volume recorded.

Saturated ammonium sulfate can be added dropwise to the supernatant with stirring. The material precipitating between 35 and 60% saturated ammonium sulfate can be collected by centrifugation (10 k Xg×30 minutes). The resulting pellet is resuspended in a buffer containing 10 mM sodium phosphate, pH 7.0, 1 mM $Na_2$-EDTA, 0.1 mM DDT, 10 μM leupeptin and 20% glycerol (equilibration buffer) and the volume recorded.

The resuspended material can be applied to a column (1×15 cm) containing DEAE-Sepharose (Sigma Chem. Co., St. Louis, Mo.) previously equilibrated with equilibration buffer and 1.0 ml fractions collected. An additional two-column volume of equilibration can be passed through the column. A linear gradient of NaCl (0–0.3M, Σ ml) in equilibration buffer can be applied to the column. The fractions can be monitored for absorbance at 280 nm and the peak fractions analyzed by SDS PAGE and enzyme assay. Fractions enriched in ecdysone oxidase activity and protein can be pooled and dialyzed against equilibration buffer.

The dialyzed material an be applied to a column (1×15 cm) containing CM-Sepharose (Sigma Chem. Co., St. Louis, Mo.) previously equilibration buffer and 1.0 ml fractions collected. An additional two column. volumes of equilibration can be passed through the column. A linear gradient of NaCl (0–0.3M, Σ ml) in equilibration buffer can be applied to the column. Once again, the fractions can be monitored for their absorbance at 280 nm and the peak fractions analyzed by SDS PAGE and enzyme assay. Fractions enriched in ecdysone oxidase activity and protein can be pooled and dialyzed against a buffer containing equilibration buffer.

EXAMPLE 2

Protein Determination and Polyacrylamide Gel Electrophoresis

Protein concentrations can be determined according to the method of Bensadoun and Weinstein (Bensadoun, et al., 1976) using bovine serum albumin as the protein standard. Polyacrylamide gel electrophoresis can be performed in the presence of sodium dodecyl sulfate (SDS PAGE) essentially as described (Laemmli, 1970).

EXAMPLE 3

Enzyme Assays

A typical reaction mixture contains between 0.05–2 mg of the enzyme and 50 mM potassium phosphate buffer, pH 7.0 in a final volume of 1.0 ml. Following a preincubation of 3 minutes at 30° C., the reaction can be initiated by the addition of 10–50 μM α-[23,24-$^3$H(N)]-ecdysone or [24,24, 26,27-$^3$H(N)]-ponasterone A (Dupont NEN®, Boston, Mass.). Incubations can be allowed to proceed 5–60 minutes at 30° C. with shaking at 60 oscillations minutes$^{-1}$ in a Model 976 gyrorotary water bath (New Brunswick Scientific, Edison, N.J.). The reaction can be stopped by the extraction of ecdysone or ponasterone A and their respective metabolites in 9.0 ml chloroform. Following centrifugation at 2500 Xg×5 minutes, the aqueous phase can be removed by aspiration and an aliquot of the organic phase containing ecdysone, and metabolites thereof are dried under a stream of nitrogen. The residue can be redissolved in 25 μl ethyl acetate and applied to a sheet of IB2-F silica gel (J. T. Baker, Phillipsburg, N.J.). The thin layer sheets can be developed by sequential chromatography with chloroform:ethanol (9:1) and ethyl acetate:cyclohexane (1:1). The parent substrate and its metabolites can be visualized by radioautography and the areas of the silica gel containing the compounds of interest removed and quantitated using a liquid scintillation analyzer (Packard Instrument Co., Laguna Hills, Calif.). The identification of 3-dehydroecdysone and 3-dehydro-20-hydroxyecdysone can be made by a direct comparison of the relative mobility with that of authentic 3-dehydroecdysteroids.

EXAMPLE 4

Bioassay of Ecdysone Oxidase as a Pesticidal Agent

Neonate diamondback moth (*Plutélla xylostélla*) larvae can be collected after hatch and starved for 18 hours. Droplets of a solution of water containing dye and purified ecdysone oxidase (0–0.1 mg ml$^{-1}$) can be placed in an array on a petri dish. The larvae can be placed in the dish and allowed access to the solution. After approximately 30 minutes larvae can be examined microscopically for dye in the midgut, and these larvae can be placed on an artificial diet in which ecdysone oxidase is incorporated (0–0.1 mg ml$^{-1}$). Each day following ingestion of the diet by diamondback moth, the larvae are scored for stunting. Three to five days following initial infestation, the larvae can be weighed and compared to the control group.

EXAMPLE 5

Insertion of Toxin Genes Into Plant

One aspect of the subject invention is the transformation of plants with genes encoding a protein which disturbs ecdysteroid metabolism in pests that ingest portions of the plant. The transformed plants are resistant to attack by pests.

A gene encoding the pest-controlling protein can be inserted into plant cells using a variety of techniques which are well known in the art. Those techniques include transformation with T-DNA using *Agrobacterium tumefaciens* or *Agrobacterium rhizogenes* as transformation agent, fusion, microinjection, particle bombardment (biolistics), chemical agent (PEG) assisted DNA uptake, or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters et al., 1978). The Agrobacterium used as host cell is to comprise a plasmid carrying a vir region. The vir region is necessary for the transfer of the T-DNA into the plant cell.

The use of T-DNA for the transformation of plant cells has been intensively researched and sufficiently described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

The bacterium so transformed is used for the transformation in plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts, callus cells, or suspension-cultivated cells) in a suitable medium, which may contain antibiotics or biocides for selection. The plants so obtained can then be tested for the presence of the inserted DNA. No special demands are made of the plasmids in the case of microinjection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting progeny have the corresponding phenotypic properties.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

United States Patents
 U.S. Pat. No. 4,695,455.
 U.S. Pat. No. 4,695,462.
 U.S. Pat. No. 5,380,831
International and Foreign Patents and Applications
 EP 120 516
Other Publications An et al. (1985) *EMBO J.* 4:277–287.

Bensadoun, A., D. Weinstein (1976) *Anal. Biochem.* 70:241–250.

Corbin, D. R., et al (1994) "Cloning of an Insecticidal Cholesterol Oxidase Gene and its Expression in Bacteria and in Plant Protoplasts," *Appl. Environ. Microbiol* 60:4239–4244.

Fraley et al., *Crit. Rev. Plant Sci* 4:1–46.

Gilbert and Goodman (1981) Chapter 5: "Chemistry, Metabolism, and Transport of Hormones Controlling Insect Metamorphosis" (subsection: "Molting Hormone") in *Metamorphosis: A Problem in Developmental Biology*, Gilbert, L. I. and E. Frieden, eds., Plenum Press, N.Y., pp. 139–173.

Holsters et al (1978) *Mol. Gen. Genet.* 163:181–187.

Hoekema (1985) In: *The Binary Plant Vector System*, Offset-durkkerij Kanters B. V., Alblasserdam, Chapter 5.

Humason, Gretchen L. (1967) *Animal Tissue Techniques*, W. H. Freeman and Company.

Laemmli, U. K. (1970) *Nature* 227:680–685.

Purcell, J. P., et al. (1994) "Cholesterol Oxidase: A Potent Insecticidal Protein Against Boll Weevil Larvae," *Biochem. Biophys. Res. Comm.* 196:1406–1412.

Tanaka, Y., Takeda, S. (1993) "Ecdysone and 20-hydroxyecdysone Supplements to the Diet Affect Larval Development in the Silkworm, *Bombyx mori*, Differentially." *J. Insect Pathol.* 39:805–809.

I claim:

1. A method for the control of a pest selected from the group consisting of insects, mites, and nematodes, wherein said method comprises administering to said pest an effective amount of an enzyme selected from the group consisting of ecdysone oxidase and 3-oxoecdysteroid 3β-reductase.

2. The method, according to claim 1, which further comprises transforming a host to express a *Bacillus thuringiensis* δ-endotoxin and an enzyme selected from the group consisting of ecdysone oxidase and 3-oxoecdysteroid 3β-reductase, and administering said *Bacillus thuringiensis* toxin to said pest.

* * * * *

UNITED STATES PATENT AND TRADEMARK OFFICE
CERTIFICATE OF CORRECTION

PATENT NO.    :   5,753,249

DATED         :   May 19, 1998

INVENTOR(S)   :   George E. Schwab

It is certified that error appears in the above-identified patent and that said Letters Patent is hereby corrected as shown below:

Column 2, line 3: "strategies *B.t.* transgene" should read --strategies in *B.t.* transgene--.

Column 7, line 59: "column. volumes" should read --column volumes--.

Signed and Sealed this

Seventeenth Day of November, 1998

Attest:

BRUCE LEHMAN

*Attesting Officer*     *Commissioner of Patents and Trademarks*